United States Patent
Keen et al.

(10) Patent No.: US 11,116,425 B2
(45) Date of Patent: Sep. 14, 2021

(54) PACING ACTIVITY DATA OF A USER

(71) Applicant: APPLE INC., Cupertino, CA (US)

(72) Inventors: Daniel S. Keen, San Jose, CA (US); Jay C. Blahnik, San Francisco, CA (US); Gaurav Kapoor, Santa Clara, CA (US); Michael R. Siracusa, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 318 days.

(21) Appl. No.: 16/180,483

(22) Filed: Nov. 5, 2018

(65) Prior Publication Data
US 2019/0117127 A1    Apr. 25, 2019

Related U.S. Application Data

(62) Division of application No. 14/475,417, filed on Sep. 2, 2014, now Pat. No. 10,117,600.

(51) Int. Cl.
*A61B 5/00* (2006.01)
*A61B 5/11* (2006.01)
(Continued)

(52) U.S. Cl.
CPC .......... *A61B 5/1118* (2013.01); *A61B 5/4866* (2013.01); *A61B 5/7275* (2013.01);
(Continued)

(58) Field of Classification Search
CPC ............ A61B 2562/0219; A61B 5/111; A61B 5/1118; A61B 5/112; A61B 5/4843;
(Continued)

(56) References Cited

U.S. PATENT DOCUMENTS

| 6,145,389 A * | 11/2000 | Ebeling | A61B 5/1038 |
| | | | 73/865.4 |
| 6,213,872 B1 * | 4/2001 | Harada | A63B 24/00 |
| | | | 463/7 |

(Continued)

FOREIGN PATENT DOCUMENTS

| WO | 2006072961 | 7/2006 |
| WO | 2016036486 | 3/2016 |

OTHER PUBLICATIONS

Non-Final Office Action issued in U.S. Appl. No. 14/475,417, dated Jun. 19, 2017 in 12 pages (of-record in parent application).
(Continued)

*Primary Examiner* — May A Abouelela
(74) *Attorney, Agent, or Firm* — Kilpatrick Townsend & Stockton LLP

(57) ABSTRACT

Pacer activity data of a user may be managed. For example, historical activity data of a user corresponding to a particular time of a day prior to a current day may be received. Additionally, a user interface configured to display an activity goal of the user may be generated and the user interface may be provided for presentation. In some aspects, the user interface may be configured to display a first indicator that identifies cumulative progress towards the activity goal and a second indicator that identifies predicted cumulative progress towards the activity goal. The cumulative progress may be calculated based on monitored activity from a start of the current day to the particular time of the current day and the predicted cumulative progress may be calculated based on the received historical activity data corresponding to the particular time of the day prior to the current day.

20 Claims, 11 Drawing Sheets

(51) Int. Cl.
    *G06F 9/54*           (2006.01)
    *G06F 9/48*           (2006.01)
    *G06F 8/65*           (2018.01)

(52) U.S. Cl.
    CPC .............. *G06F 8/65* (2013.01); *G06F 9/4843* (2013.01); *G06F 9/4893* (2013.01); *G06F 9/542* (2013.01); *G06F 2209/482* (2013.01); *Y02D 10/00* (2018.01)

(58) Field of Classification Search
    CPC ....... A61B 5/4866; A61B 5/7275; G06F 8/65; G06F 9/4843; G06F 9/542; G06F 9/4893; G06F 2209/482; Y02D 10/00
    USPC ............ 600/300, 587, 595; 700/91; 709/206
    See application file for complete search history.

(56) References Cited

U.S. PATENT DOCUMENTS

| | | | | |
|---|---|---|---|---|
| 7,559,877 | B2* | 7/2009 | Parks | A63B 69/0028 |
| | | | | 482/3 |
| 7,789,802 | B2* | 9/2010 | Lee | G07C 1/10 |
| | | | | 482/8 |
| 8,515,499 | B1* | 8/2013 | Stekkelpak | G06F 1/3212 |
| | | | | 455/566 |
| 8,961,414 | B2* | 2/2015 | Teller | G16H 20/30 |
| | | | | 600/301 |
| 9,031,812 | B2* | 5/2015 | Roberts | G06F 15/00 |
| | | | | 702/160 |
| 9,310,909 | B2* | 4/2016 | Myers | A61B 5/7264 |
| 10,117,600 | B2 | 11/2018 | Keen et al. | |
| 2003/0176815 | A1* | 9/2003 | Baba | A61B 5/02438 |
| | | | | 600/595 |
| 2007/0179739 | A1* | 8/2007 | Donofrio | A61B 5/1123 |
| | | | | 702/160 |
| 2007/0225118 | A1 | 9/2007 | Giorno et al. | |
| 2009/0018797 | A1* | 1/2009 | Kasama | G01C 22/006 |
| | | | | 702/160 |
| 2009/0299691 | A1* | 12/2009 | Shimaoka | G01C 22/006 |
| | | | | 702/160 |
| 2010/0304674 | A1* | 12/2010 | Kim | H04W 76/10 |
| | | | | 455/41.2 |
| 2012/0015778 | A1* | 1/2012 | Lee | A63B 71/0686 |
| | | | | 482/8 |
| 2013/0325396 | A1* | 12/2013 | Yuen | A61B 5/0002 |
| | | | | 702/160 |
| 2014/0085077 | A1* | 3/2014 | Luna | A61B 5/7455 |
| | | | | 340/539.11 |
| 2014/0121471 | A1* | 5/2014 | Walker | A61B 5/11 |
| | | | | 600/301 |
| 2014/0200691 | A1* | 7/2014 | Lee | A61B 5/1118 |
| | | | | 700/91 |
| 2014/0316305 | A1* | 10/2014 | Venkatraman | A61B 5/681 |
| | | | | 600/595 |
| 2014/0337451 | A1* | 11/2014 | Choudhary | G08B 6/00 |
| | | | | 709/206 |
| 2015/0057967 | A1* | 2/2015 | Albinali | A61B 5/1118 |
| | | | | 702/150 |
| 2015/0198460 | A1* | 7/2015 | Yamato | A61B 5/681 |
| | | | | 702/160 |
| 2015/0324541 | A1* | 11/2015 | Cheung | G16H 50/30 |
| | | | | 705/2 |
| 2015/0374267 | A1* | 12/2015 | Laughlin | A61B 5/1118 |
| | | | | 702/19 |
| 2016/0058331 | A1 | 3/2016 | Keen et al. | |

OTHER PUBLICATIONS

Non-Final Office Action issued in U.S. Appl. No. 14/475,417, dated Jan. 22, 2018 in 13 pages (of-record in parent application).

Notice of Allowance issued in U.S. Appl. No. 14/475,417, dated Jul. 9, 2018 in 11 pages (of-record in parent application).

Restriction Requirement issued in U.S. Appl. No. 14/475,417, dated Feb. 1, 2017 in 12 pages (of-record in parent application).

International Preliminary Report on Patentability issued in PCT Application No. PCT/US2015/044882, dated Mar. 16, 2017 in 8 pages (of-record in parent application).

International Search Report and Written Opinion issued in PCT Application No. PCT/US2015/044882, dated Oct. 15, 2015 in 10 pages (of-record in parent application).

* cited by examiner

PACING ACTIVITY DATA OF A USER

CROSS REFERENCE TO RELATED APPLICATIONS

The present application is a divisional of U.S. Non-Provisional application Ser. No. 14/475,417, filed on Sep. 2, 2014, entitled "Pacing Activity Data of a User," which is hereby incorporated by reference and for all purposes. The present application is related to U.S. Non-Provisional application Ser. No. 14/253,742, filed on Apr. 15, 2014, entitled "Dynamic Adjustment of Mobile Device Based on User Activity," by Stanley-Marbell, et. al and U.S. Provisional Application Ser. No. 62/005,940, filed on May 30, 2014, entitled "Dynamic Adjustment of Mobile Device Based on System Events," by Stanley-Marbell, et. al, the entire contents of each are hereby incorporated by reference as if fully set forth herein, under 35 U.S.C. § 120.

BACKGROUND OF THE INVENTION

People are becoming more and more aware of the importance of regular exercise for maintaining one's health. Additionally, a plethora of electronic devices are now available that can track a person's physical activity throughout the day. Such devices can connect or otherwise communicate with other mobile devices, for example, to help track, manage, and/or analyze data associated with the person's physical activity. However, health and activity data may not always provide meaningful information to users. As such, developers and device manufacturers continue to identify challenges when providing applications and/or devices for collecting and sharing a user's health information.

BRIEF SUMMARY OF THE INVENTION

Embodiments of the present disclosure can provide systems, methods, and computer-readable medium for pacing activity data of a user. In some examples, a data collection device may collect activity data of a user and provide a user interface for measuring the user's level of completion of a goal. Additionally, a pace of the user may be calculated based at least in part on historical activity data and a pacer element may be represented on the user interface to indicate the user's relative level of activity with respect to the pacer element. In this way, the user may gauge his or her activity level in terms of what they have done historically at any given point in time.

According to one embodiment, a system may be implemented as a computing device configured with a memory and a processor. The processor may be configured to execute instructions stored on the memory to determine a predicted amount of activity of a user for at least one interval of a time period. The processor may also be configured to execute the instructions to identify an activity goal of the user for the time period and/or to collect current activity data of the user for a current interval of the time period. Further, in some examples, the processor may be configured to execute the instructions to provide a user interface capable of presenting a pace of the user with respect to the collected current activity data as at least a portion of the activity goal for the time period. The pace of the user may be based at least in part on the predicted amount of activity for the current interval.

In some examples, the activity may be capable of being tracked cumulatively. The predicted amount of activity may be based at least in part on a probability that the user will meet a threshold activity level during the at least one interval. The at least one interval may comprise the current interval and/or the predicted amount of activity may be based at least in part on historical activity data of the user. In some cases, the at least one interval or the current interval may comprise an hour of time. The identified activity goal may be received from the user. Additionally, the current activity data may be collected by an activity tracking device in communication with the processor and may be configured to provide the current activity data for storage in the memory. Further, the processor may be further configured to execute the computer-executable instructions to at least receive the current activity data from a computing device external to the system.

According to another embodiment, a method may be executed by a computer system to at least receive, from a first computing device, historical activity data of a user from a second computing device configured to collect the historical activity data. The method may also cause the computer system to provide the received historical activity data to a service provider configured to predict future activity data of the user. The computer system may receive, from the service provider, the predicted future activity data. In some cases, the predicted future activity data may identify an interval of a time. The method may also cause the computer system to receive current activity data of the user collected by the second computing device during a current interval of time that corresponds to the identified interval of time. In some examples, the computer system may identify an activity goal of the user and/or provide, to the second computing device, information for configuring a user interface of the second computing device to present the activity goal, the current activity data for the current interval, and the predicted future activity data for the current interval.

In some cases, the user interface of the second computing device may be configured to present a first graphical representation of the current activity data and the predicted future activity data overlaid on a second graphical representation of the activity goal. The first graphical representation may be configured to present the current activity data adjacent to the predicted future activity data. In some examples, the current interval may comprise an hour of a day in which the current activity data is detected. Additionally, the historical activity data may comprise calories burned by the user, heart beats of the user, steps walked by the user, distance traveled by the user, or minutes exercised by the user.

According to another embodiment, a computer-readable medium may include instructions that, when executed, configure a computer processor to perform operations comprising receiving, from a data collecting device, activity data of a user. The activity data may comprise historical activity data and current activity data. In some cases, the operations may further comprise identifying predicted activity data of the user for an interval of a time period. The predicted activity data may be based at least in part on the historical activity data. the operations may also comprise receiving, from the user, an activity goal for the time period and/or preparing a user interface configured to present the predicted activity data and the current activity data as separate indicators of portions of the activity goal for at least the interval of the time period.

In some examples, the data collecting device is configured to identify user activity of the user and generate the activity data based at least in part on the identified user activity. In some cases, the operations may further comprise providing the historical activity data to a service provider configured to determine a probability of an amount of activity for at least the time interval and/or receiving, from the service provider, the predicted activity data. The predicted activity data may be based at least in part on the determined probability of the amount of activity for at least the time interval. Further, the user interface may be provided to the data collection device for presentation to the user.

According to another embodiment, a method may be executed by a computer system to at least receive historical activity data of a user corresponding to a particular time of a day prior to a current day. The method may also cause the computer system to generate a user interface configured to display an activity goal of the user. In some cases, the user interface further configured to display a first indicator that identifies cumulative progress towards the activity goal and a second indicator that identifies predicted cumulative progress towards the activity goal. The cumulative progress may be calculated based at least in part on monitored activity from a start of the current day to the particular time of the current day. The predicted cumulative progress may be calculated based at least in part on the received historical activity data corresponding to the particular time of the day prior to the current day. The method may also cause the computer system to provide the user interface for presentation to a computing device of the user.

In some cases, the historical activity data may comprise a number of calories burned. The user interface may be configured to be presented as a bar or line. Further, in some examples, the user interface is configured to be presented as a circle or oval.

DETAILED DESCRIPTION OF THE INVENTION

Figure 1:
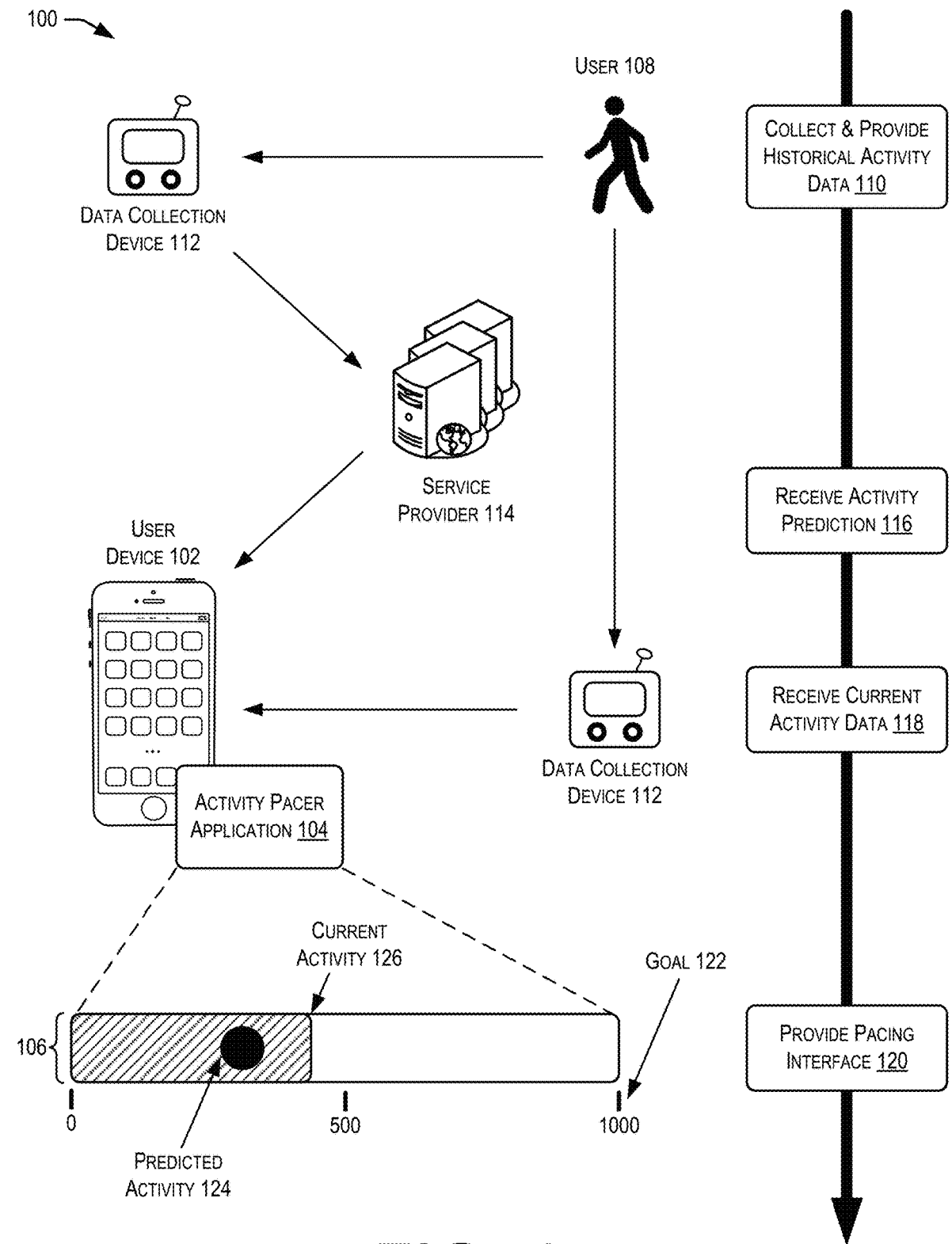
FIG. 1 is a simplified block diagram illustrating an example flow for managing pacer activity data of a user as described herein, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, managing cumulative health data collected by one or more data collection devices of a user and providing pacing activity data of the user. In particular, the cumulative health data may be presented to a user as part of a user interface and/or pacer application configured to present a user's cumulative total activity information for a particular time period along with (e.g., adjacent to) a predicted amount of activity information for that time period. Additionally, this activity information, (e.g., the cumulative actual total and/or the predicted total) may be presented as indicators, and may indicate or otherwise identify a percentage, subset, or portion of a user's goal for that time period. For example, a user may set 1000 steps as a goal for walking in a particular day. As the user walks during that particular day, a data collection device may be configured to collect or identify the number of steps that the user takes. At each moment in time during that day, a user interface (e.g., presented on the data collection device or another user device) may be configured to display the cumulative number of steps walked up to that moment with relation to the goal of 1000 steps. Additionally, in some examples, the user device, a third-party service provider, or another device (e.g., of the user) may determine a probability and/or prediction of a total number steps walked by that user up to that moment. This prediction may be based at least in part on historical walking data of the user. As such, the user interface may also be configured to present this predicted number of steps adjacent to, at the same time as, and/or on top of the actual cumulative number of steps walked up to that point. The predicted number of steps for each moment may be called the "pace" of the user, and may indicate whether the user is currently ahead or behind of their predicted pace for the day.

In one example, a user may utilize a data collection device such as a pedometer, a heart-rate monitor, or the like to collect and/or track the number of calories the user burns each day. The user may also utilize a mobile phone or other portable electronic device that may interact with the data collection device. The data collection device may be configured to communicate with one or more other devices, such as a server, a service provider, and/or the user device. In some cases, the data collection device or the user device may send the collected data to a third-party service that can attempt to predict the amount of calories that the user may burn based on the collected data. As such, the service may provide a predicted number of calories that the user is expected to burn for each hour of the next day based on the historical data collected over time. On the following day, the user may view a user interface of the user device or data collection device and set a goal for the day. For example, the user may set a goal of 1000 calories burned. Based on the predicted number of calories received from the third-party service, the user interface may indicate that the user is expected to reach 200 calories burned (20% of her goal) by lunch time because the user doesn't usually exercise much until after lunch. Additionally, throughout the day, the user's calorie tracker may collect actual activity data and may be able to present the actual calories burned by the user at any given time. In this example, if the user has actually burned 300 calories by lunch (30% of her goal), the user interface may be configured to show the user's "pace" (e.g., predicted number) and the user's actual number of calories burned with respect to the goal for the day. In this way, the user will be able to see that she is ahead of her pace at lunchtime, even though she is only at 30% of the goal.

In some cases, a probability graph may be generated based at least in part on historical activity data collected for a user. The probability graph may identify a probability, for each time of a day, that a user will reach a certain level of (e.g., a maximum) cumulative activity data collected. In other words, the probability graph may illustrate what the user's collected activity data is expected to resemble and/or the maximal likelihood activity data collected for any given moment in time (e.g., the attribute value with the highest probability may be provided). For example, if a user typically exercises on Monday mornings, the probability graph may show a high probability that during the morning hours on Monday, the user may have accumulated a higher than average (or at least higher than during other parts of the day) value for the activity. Alternatively, the probability graph may identify a maximal likelihood of activity for each moment in time, such that the highest probability for each hour of Monday morning will indicate a higher level of activity than the highest probability for each hour of Monday afternoon. Similarly, if that user doesn't typically exercise on Tuesdays, the probability graph may show a low probability of similar values collected for that activity with respect to Monday or it may show that the highest probability for Tuesday morning hours is much less than that for Monday. While activity data collection may typically be expected at all times, the probability graph may indicate relative probabilities with respect to relative levels or amounts of accumulated activity attribute values. As noted, activity data may be collected by one or more data collection devices and values may include steps walked, calories burned, distance ran (or walked), number of activity types conducted (e.g., reps of an exercise or the like), or any other activity, event, or action that may be collected about a user.

In some examples, the probability graph may be based at least in part on historically collected activity data of the user. Further, the probability graph may be generated and/or provided by a third-party service or other service external to the data collection device and/or user device of the user. For example, a service provider may receive the activity data collected from the data collection device, generate the probability graph based at least in part on that received data, and then provide the probability graph to the user device and/or data collection device. In this scenario, the data collection device and/or user device may be configured to provide the user interface that incorporates the actual data collected (e.g., cumulative steps for the day up to the current time) and an indicator of the predicted amount of data expected (e.g., the predicted number of steps based at least in part on the probability graph for that current time). Additionally, these two data points (i.e., the actual collected data and the predicted data) may be provided as at least an indication of a portion of the user's goal for the day. Further, in some examples, the predicted amount of collected activity data may be based at least in part on the probability graph. In some examples, the predicted amount may be a cumulative integral of the probability graph. This predicted amount may be presented as a user interface element (e.g., a pacing dot).

The pacing dot or other user interface element that is to be provided with the actual cumulative amount of activity data collected may be determined mathematically by summing the cumulative amount of predicted activity data points for any given time. In other words, if calorie burn rate is being calculated, the probability graph may provide a set of probabilities for each time interval (e.g., an hour) over a time period (e.g., a day) of a predicted calorie burn rate. From this predicted calorie burn rate for each time interval, the cumulative integral may provide a predicted cumulative amount of calories burned for those time intervals. At any given time interval, this cumulative integral may identify the pace at which the user is expected be burning calories (or any other collected data type). Thus, the user interface may provide this pace (e.g., as a dot or other indicator) on a graph or other representation of the user goal. The actual amount of cumulative calories burned (e.g., collected by a data collection device) may also be presented next to, on top of, or otherwise adjacent to the pacing dot indicating to the user whether she is currently behind or ahead of her goal for the day.

In some examples, a service provider may be configured to provide a user interface with an indicator that displays cumulative daily progress (e.g., calories burned or the like) towards a goal. The cumulative daily progress may be cumulative with respect to the start of the day up to a current time of day. Additionally, the user interface may also include another indicator that displays a predicted cumulative daily progress for the same time of day, for at least one day occurring before the current day. In some cases, the service provider may receive historical activity data of a user corresponding to a particular time of day. For example, the service provider may receive information indicating that the user burned 50 calories by 11 am on the previous day, or by 11 am on a previous Tuesday. The service provider may then generate a user interface that displays an activity goal of the user (e.g., 1000 calories burned) along with a first indicator that displays that by 11 am of the current day (e.g., today), the user has burned 100 calories or 10% of the goal. The user interface may also display another indicator that displays that by 11 am of the current day, the users predicted accumulated activity level would be 50 calories based at least in part on the historical data that indicated that the user had burned 50 calories by 11 am previously. The user interface may then be provided to a computing device of the user.

The service provider (e.g., third-party, external, or internal) may monitor and/or receive system-defined and client-defined attributes and can use the system-defined and client-defined attributes to predict or forecast the occurrence of future events (e.g., user activity). This service can anticipate the user's future behavior based at least in part on dynamically gathered statistics and/or explicitly specified user intent. In some examples, the service may be configured to determine probabilities of future levels of activity of the user. In some implementations, the service can include a sampling daemon that collects events related to user activity, network conditions, system services (e.g., daemons), and/or other user behavior. For example, the sampling daemon can collect statistics related to applications, sensors, and user input received by user device and/or data collection device, and store the statistics in an event data store. The statistics can be reported to the sampling daemon by various clients (e.g., applications, utilities, functions, third-party applications, etc.) running on the mobile device using predefined or client-defined attributes reported as events.

In some implementations, the service can be configured with a framework for collecting system and/or application events. For example, service can be configured with application programming interfaces (APIs) that allow various applications, utilities, and other components of mobile device to submit events to the sampling daemon for later statistical analysis. Additionally, each event recorded by the sampling daemon in the event data store can include an attribute name (e.g., "CaloriesBurned"), an attribute value (e.g., "100"), anonymized beacon information, anonymized location information, date information (e.g., GMT date of event), time information (e.g., localized 24 hour time of event), network quality information, processor utilization metrics, disk input/output metrics, identification of the current user, and/or type of event (e.g., start, stop, cumulative amount, etc.). For example, the attribute name can identify the type of attribute associated with the event. The attribute name can be used to identify a particular metric being tracked by the sampling daemon, for example. The attribute value can be a value (e.g., string, integer, floating point) associated with the attribute. The anonymized beacon information can indicate which wireless beacons (e.g., Bluetooth, Bluetooth Low Energy, Wi-Fi, etc.) are in range of the mobile device without tying or associating the beacon information to the user or the device. Similarly, the anonymized location information can identify the location of the mobile device without tying or associating the location information to the user or the device. For example, location information can be derived from satellite data (e.g., global positioning satellite system), cellular data, Wi-Fi data, and/or Bluetooth data using various transceivers configured on mobile device. Network quality information can indicate the quality of the mobile device's network (e.g., Wi-Fi, cellular, satellite, etc.) connection as detected by the mobile device when the event occurred.

In some implementations, the event data for each event can indicate that the event occurred, started, stopped, and/or or a level of activity. For example, time accounting (e.g., duration accounting) can be performed on pairs of events for the same attribute that indicate a start event and a stop event for the attribute. For example, the sampling daemon can receive an event for attribute "CaloriesBurned" having a value "100." Later, the sampling daemon can receive another event for attribute "CaloriesBurned" having a value "200." The sampling daemon can compare the time of the start event to the time of the stop event to determine how many calories were burned during that time period. In some implementations, events that are not subject to time accounting can be recorded as point events (e.g., a single occurrence). For example, an event associated with the "batteryLevel" system attribute that specifies the instantaneous battery level at the time of the event can simply be recorded as an occurrence of the event. The attribute event information can be used, for example, to forecast user activity related to events performed by the user associated with the mobile device.

In some examples, the sampling daemon can receive event information from applications on the mobile device. For example, applications on the mobile device can generate events that include predefined or dynamically defined attributes to the sampling daemon to track various application-specific events. For example, the sampling daemon can receive user activity events (e.g., calories burned, steps walked, etc.) from the mobile device or data collection device. The user activity events can include attributes that have values that specify locations, times, or other data associated with various user activity events or functions. The sampling daemon can store the attribute name, attribute duration, and/or time when the attribute occurred, for example.

In some implementations, a temporal forecast can be generated for an attribute or attribute value. The temporal forecast can indicate, for example, what values for the attributes are likely to occur at what times of the day and/or at what time of day an event associated with the attribute or attribute value is likely to occur. For example, a client of the sampling daemon can request a temporal forecast for the attribute (e.g., calories burned) over the last week (e.g., last 7 days). To generate the forecast, a 24-hour day can be divided into 96 15-minute timeslots. For a particular timeslot (e.g., 1:00-1:15 pm) on each of the last seven days, the sampling daemon can determine how many calories were burned during each time slot and generate a score for each timeslot that indicates the maximal expected calorie burn. In some implementations, the temporal forecast can be generated based on an event history window specification. For example, if the client provides a window specification that specifies a 4-hour time period of interest, the temporal forecast will only generate likelihood scores for the 15-minute timeslots that are in the 4-hour time period of interest. For example, if the time period of interest corresponds to 12:00-4:00 pm for each of the last 3 days, then 16 timeslots will be generated during the 4 hour period of interest and a score will be generated for each of the 16 15 minute timeslots. Scores will not be generated for timeslots outside the specified 4 hour time period of interest.

In some implementations, the sampling daemon can generate peer forecasts for attributes. For example, a peer forecast can indicate the relative likelihoods of values for an attribute occurring during a time period of interest relative to all values of the same attribute. For example, a client of the sampling daemon can request a peer forecast of the "CaloriesBurned" attribute over a time period of interest (e.g., 11:00 am-1:00 pm) as specified by a window specification submitted with the request. If, during the time period of interest, "CaloriesBurned" events having attribute values "100," "300," "400," "200," "100," "200," "100" occur, then the relative likelihood (i.e., score) of "100" occurring is 0.43 (e.g., 3/7), the relative likelihood of "200" occurring is 0.29 (e.g., 2/7) and the relative likelihoods for "300" or "400" occurring is 0.14 (e.g., 1/7).

In some implementations, a client of the sampling daemon can request a peer forecast for an attribute. For example, if a client requests a peer forecast for an attribute without specifying a value for the attribute, then the sampling daemon will generate a peer forecast and return the various probability scores for all values of the attribute within the time period of interest. Using the example peer forecast above, sampling daemon 102 will return a list of attribute values and scores to the requesting client, for example: "100":0.43; "200":0.29; "300":0.14; "400":0.14.

In some implementations, a client of the sampling daemon can request a peer forecast for an attribute value. For example, the client can request a peer forecast for the "CaloriesBurned" attribute having a value of "100." The sampling daemon can generate a peer forecast for the "CaloriesBurned" attribute according to the window specification provided by the client, as described above. For example, the sampling daemon can calculate the relative likelihood (i.e., score) of "100" occurring is 0.43 (e.g., 3/7), the relative likelihood of "200" occurring is 0.29 (e.g., 2/7) and the relative likelihoods for "300" or "400" occurring is 0.14 (e.g., 1/7). The sampling daemon can return a score for the requested "100" value (e.g., 0.43) to the client. If the requested value is not represented in the time period of interest as specified by the window specification, then a value of zero will be returned to the client. Additional details of the service provider and/or the sampling daemon can be found in U.S. Non-Provisional application Ser. No. 14/253, 742, filed on Apr. 15, 2014, entitled "Dynamic Adjustment of Mobile Device Based on User Activity," by Stanley-Marbell, et. al and U.S. Provisional Application Ser. No. 62/005,940, filed on May 30, 2014, entitled "Dynamic Adjustment of Mobile Device Based on System Events," by Stanley-Marbell, et. al, the entire contents of each are hereby incorporated by reference as if fully set forth herein, under 35 U.S.C. § 120. While these two applications discuss the sampling daemon mostly with respect to activity events such as application invocation and the like, it should be understood that any type of data including cumulative-type user activity data (e.g., calories burned, steps walked, distance traveled, etc.) may be forecasted and/or predicted in a similar fashion.

While examples are given where a data collection device is configured to collect data and interact with a different user device (e.g., a mobile phone, tablet, or the like), it should be understood that any configuration of devices may be used to implement the embodiments described here. For example, a single user device may be configured to collect the actual activity data of the user, determine the predicted amount of activity data collected, receive and/or manage the user goal, and provide a user interface that incorporates all three data points (e.g., the actual data, the predicted data, and the goal) at any given time. Additionally, in other examples, multiple data collection devices (e.g., each collecting different activity data) may provide sets of activity data that may be aggregated into a single goal and/or user interface for indicating relative levels of reaching that goal. For example, a first data collection device may collect steps walked, while another device may collect a user's speed or distance traveled. These two types of data could possibly be aggregated to create some separate data type (e.g., calories burned) and could be used to present the calories burned goal along with the pace and actual data collected.

FIG. 1 illustrates a simplified flow diagram 100 depicting a user device 102 configured with an activity pacer application 104, or the like, that may provide a user interface 106 to a user 108 of the user device 102. In some examples, at 110 of the flow 100, a data collection device 112 may be configured to collect activity data of the user 108 (e.g., while the user 108 is exercising, walking to work, etc.). Additionally, the data collection device 112 may also be configured to provide the collected activity data (e.g., historical activity data over a time period, which may include data for a current time period) to a service provider 114 or other computing system at 110 of the flow 100. The service provider 114 may comprise one or more computing systems, servers, or the like that may be configured to determine a probability graph and/or predicted amounts of activity of the user 108 for given intervals of each day (or other time periods). At 116 of the flow 100, the user device 102 may receive an activity prediction from the service provider 114. As noted, the activity prediction may be based at least in part on the historical activity data collected and/or provided by the data collection device 112.

In some examples, the data collection device 112 may continue to collect activity data of the user 108 throughout the day. As such, at any given point in time (e.g., at 118 of the flow 100), the user device 102 may receive current or actual activity data for that point in time. At least in response to a request to view progress of the user 108 towards her activity goal, the user device 102 may provide the pacing interface 106 at 120 of the flow 100. For example, the pacing interface 106 may be a bar that represents the activity goal 122 of the user 108. The pacing interface 106 may also represent the predicted activity 124 (e.g., the pacing dot) and/or the current activity level 126 of the user with respect to the goal 122. In this way, the user 108 may be able to see that while she has not reached the goal 122 of 1000 calories burned, she is at least ahead of the pace 124 for the given moment during the day (e.g., because the current activity level 126 is closer to the goal 122 and/or ahead of the predicted level 124 (e.g., the pacer dot).

Figure 2:
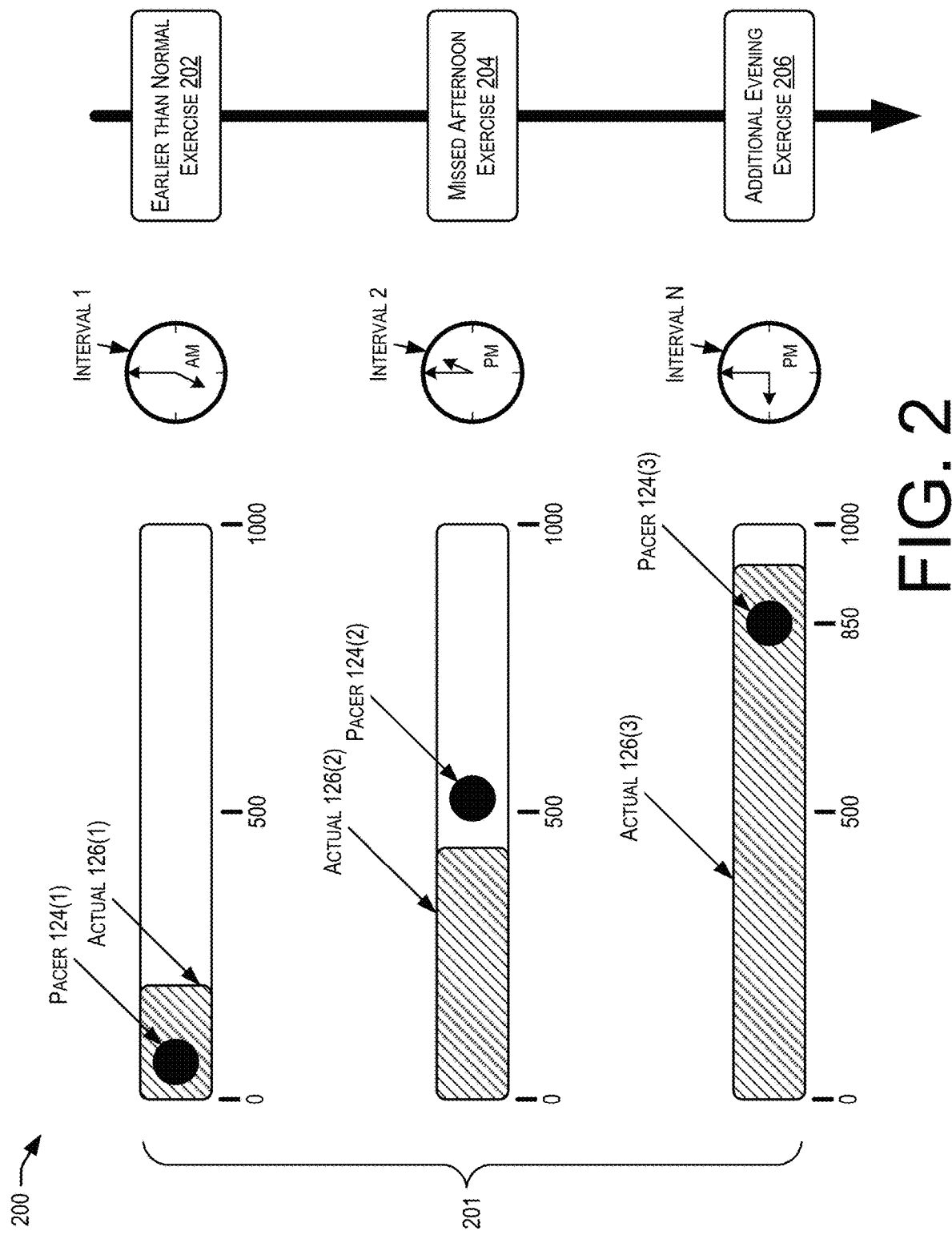
FIG. 2 is a simplified block diagram illustrating another example flow for managing pacer activity data of a user as described herein, according to at least one example.

FIG. 2 illustrates a simplified flow diagram 200 depicting additional implementation details associated with a pacer interface 201 (e.g., like the pacer application 106 of FIG. 1) and/or the activity pacer application 104 for a set of intervals 1-N of a given time period (e.g., a day). In some examples, as noted above, the pacer interface 201 may be configured to present a pacer dot 124 (e.g., based at least in part on predicted levels of activity), a cumulative activity level 126 (e.g., based on current data accumulated over a time period), and a goal 122 of a user for a given time interval 1-N or point in time. For example, at any point throughout the day, the pacer interface 201 may look different (e.g., at each interval 1-N, the current time will be different and, as such, the indicators of the interface may be different); however, the goal 122 will likely remain constant. That is, the pacer interface 201 may be configured to illustrate relative levels of activity and/or progress with respect to the goal 122. In some examples, the goal may be received from the user (e.g., through a user interface that enables the user to set the goal). The goal may be set or otherwise configured by the user to be different for each day, week, month, etc., or the goal may be set by the user to change dynamically based at least in part on some factors (e.g., the goal may increase by some amount or percentage each day or the like). Additionally, in some examples, the goal may be set dynamically, programmatically, and/or automatically based at least in part on historical activity of the user, information provided by a third-party (e.g., a doctor or health professional), and/or standards set by a group or organization. For example, a health organization and/or professional may set minimum recommended exercise standards, and the user may configure the goal to match that standard (which may change over time or based on health statistics of the user, such as height, weight, etc.).

In the simplistic example flow 200 of FIG. 2, a user may have set a goal of 1000 calories to be burned for a particular day. The flow 200 may be one illustration of an example day in which the user exercises at different times of the day than usual; thus creating data that is presented within the pacer interface 201 that illustrates instances where the user is on pace or off pace. For example, the particular user in this example may regularly not do much exercise in the morning, but may work out after lunch instead (at least on the day being tracked here). Additionally, this user may not typically reach the 1000 calories burned goal; however, they typically get to about 850 calories by 9 pm, and then go to bed. However, as can be seen by the pacer interface 201 illustrated in FIG. 2, this user exercised earlier than normal at 202 of the flow 200. As such, by 7 am, at 202, the user can see that they are ahead of pace because the actual amount of activity collected (or detected) 126(1) is ahead of the pacer dot 124(1). This may be because, as noted, the user typically does not work out in the morning, so the pacer dot 124(1) is relatively low (e.g., far from the goal) at 7 am. However, on this day, since the user exercised already, the current cumulative data (e.g., the actual activity data) 126(1) is ahead of the pacer dot 124(1).

Later in the day, at 204 of flow 200 (e.g., at 1 pm), the user may skip or otherwise miss their regular afternoon exercise. Because the user typically exercises after lunch, the activity pacer application 104 and/or the service provider 114 may have predicted for this day that the user would have surpassed the halfway point for the day's goal (e.g., 500 calories in this case). However, because the user missed their afternoon exercise, her actual activity level 126(2) may be below the pacer dot 124(2) at 1 pm. This may indicate to the user that they need to exercise more in order to get to their goal. Although they appeared to be ahead of the pace earlier in the day because of the earlier than normal exercise 202, they are now behind their predicted amount of calories burned 124(2) at 1 pm. As such, the user may choose to exercise some additional amount in the evening at 206 of flow 200. As noted above, because the user typically only completes 85% of their goal, the pacer dot 124(3) may only be at 850 by 9 pm. However, because the user exercised an additional amount at 206, their actual amount of calories burned 126(3) has surpassed the pacer dot 124(3). Thus, even though the user did not reach the goal of 1000 calories burned, they can see from the pacer interface 201 that they at least surpassed their usual (or predicted) amount of calories burned by 9 pm.

Figure 3:
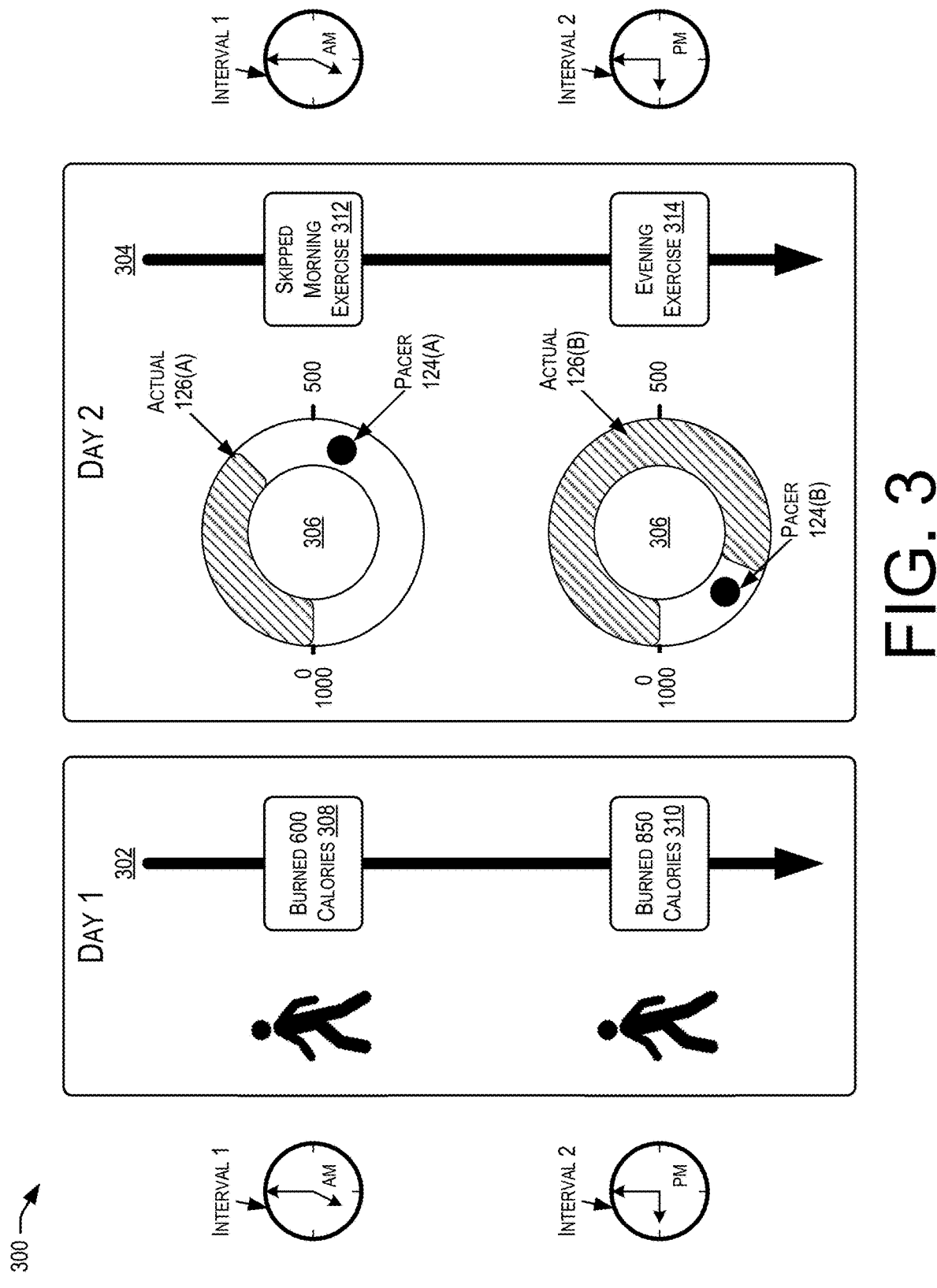
FIG. 3 is a simplified block diagram illustrating another example flow for managing pacer activity data of a user as described herein, according to at least one example.

FIG. 3 illustrates an example block diagram 300 illustrating two example flow diagrams 302, 304 depicting additional implementation details associated with a pacer interface 306 (e.g., like the pacer interface 106 of FIG. 1) and/or the activity pacer application 104 for a given time period (e.g., a day). As shown in FIG. 3, and as described above, the pacer interface 106 may take any shape or configuration (e.g., the interface 201 of FIG. 2 is depicted as a bar while the interface 306 of FIG. 3 is depicted circularly). Other shapes and/or configurations are possible without departing from the spirit of the examples provided herein. Additionally, FIG. 3 illustrates two different days, "Day 1" and "Day 2," and specific activity details associated with corresponding intervals (e.g., "Interval 1" and "Interval 2"). In this example, Interval 1 corresponds to 7 am for both Day 1 and Day, while Interval 2 corresponds to 9 pm for both Day 1 and Day 2. As such, any given interval for one day may correspond to a respective interval for another day (e.g., each interval may correspond to a particular time of the day).

In this example, the user may have cumulatively (or during that hour) burned 600 calories by or at 7 am on Day 1 as indicated by 308 of flow 302 (e.g., Interval 1). Additionally, the user may have burned a total of 850 hours by 9 pm of Day 2 as indicated by 310 of 302. As such, on Day 2, the pacer dot 124(A) may indicate a predicted amount of about 600 calories burned. However, the user may have skipped a morning workout at 312 of flow 304. As such, at 7 am, their pacer dot 124(A) may be significantly ahead of the actual amount of activity detected 126(A) because the probability graph and/or prediction expected the user to have accumulated just over 500 burned calories by that point of the day. However, because the user missed a workout that was expected, the actual number of calories burned 126(A) by 7 am was much less than 500. Additionally, on Day 2, at 9 pm, the pacer dot 124(B) may be at approximately 850 calories burned based at least in part on amount of calories burned on Day 1 or a probability associated with the amount of calories burned on Day 1 (e.g., when combined with other historical activity data for the user at 9 pm. In this example, later in the day (e.g., at 9 pm), the user may have exercised an additional amount at 314 of flow 304. However, due to the amount of predicted calories burned by the user, they did not make up the deficit, and the interface 306 still indicates that the user is behind the pace because the pacer dot 124(B) is still closer to the goal of 1000 than the actual amount of calories burned 126(B).

It should be noted that while FIG. 3 illustrates Day 1 and Day 1, Interval 1 and Interval 2, etc., any number of previous days or time periods (e.g., weeks, months, etc.) may be used for calculating and/or collecting historical activity data. For example, Day 1 may actually correspond to a Monday of a previous week or year, and Day 2 may actually correspond to a Monday of the current week. Typically, Day 2 should be understood to be the current day, and any interval of Day 2 being viewed on the user interface 306 is the current interval. For example, at 7 am on Day 2, Interval 1 is the current interval. However, by 9 pm on Day 2, Interval 2 is the current interval and Interval 1 may become part of the historical data. Further, in some examples, any time prior to the current time period (e.g., current time interval) may be considered a first time period, and the current day may be considered a second time period. As such, at a high level, predicted activity data for any interval of the current day (or the second time period) may be based at least in part on historical activity data from intervals of the first time period.

Figure 4:
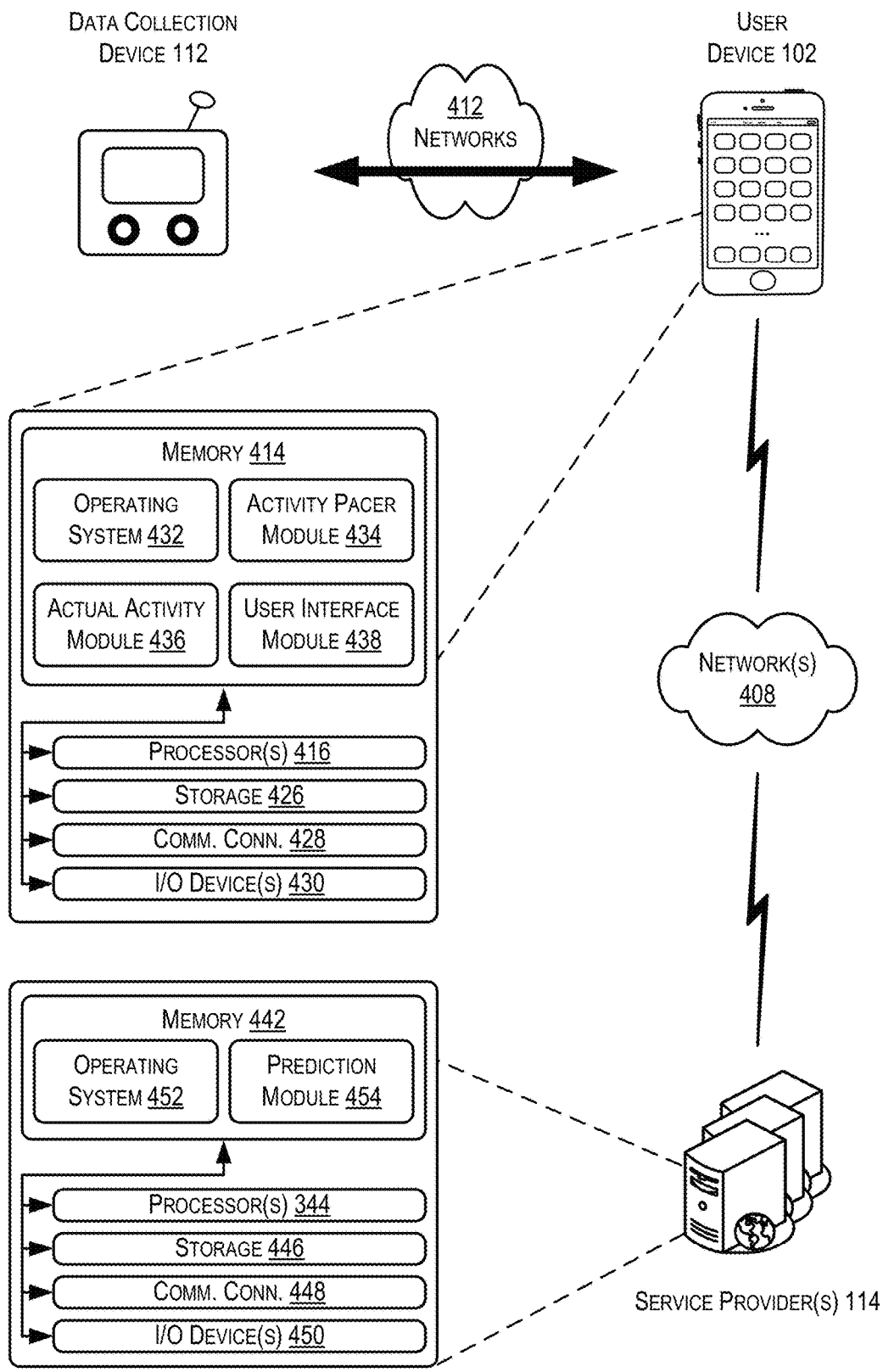
FIG. 4 is a simplified block diagram illustrating an example architecture for managing pacer activity data of a user as described herein, according to at least one example.

FIG. 4 illustrates an example architecture or environment 400 configured to implement the activity pacer application 104 and/or the pacer interface 106 of FIG. 1, according to at least one example. In some examples, the example architecture 400 may further be configured to manage or otherwise interact with the data collection devices 112, user devices 102, and/or service provider computers 114 of FIG. 1. In some examples, the devices may be connected via one or more networks 408 and/or 412 (e.g., via Bluetooth, WiFi, the Internet, or the like). In the architecture 400, one or more users may utilize the user device 102 to manage, control, or otherwise utilize the one or more data collection devices 112, via the one or more networks 412. Additionally, in some examples, the user device 102, the service provider computers 114, and the data collection device 112 may be configured or otherwise built as a single device. For example, the user device 102 and/or the data collection device 112 may be configured to implement the embodiments described herein as a single computing unit, exercising the examples described above and below without the need for the other devices described.

In some examples, the networks 408, 412 may include any one or a combination of many different types of networks, such as cable networks, the Internet, wireless networks, cellular networks, satellite networks, other private and/or public networks, or any combination thereof. While the illustrated example represents the user device 102 accessing the service provider computers 114 via the networks 408, the described techniques may equally apply in instances where the user device 102 interacts with the service provider computers 114 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the user device 102 may be configured to collect and/or manage user activity data potentially received from the data collection devices 112. In some examples, the data collection device 112 may be configured to provide health, fitness, activity, and/or medical data of the user to a third- or first-party application (e.g., the service provider 114). In turn, this data may be used by the user device 102 to present the pacer interface 106 described in FIG. 1. The user device 102 may be any type of computing device such as, but not limited to, a mobile phone, a smartphone, a personal digital assistant (PDA), a laptop computer, a desktop computer, a thin-client device, a tablet computer, a wearable device, or the like. In some examples, the user device 102 may be in communication with the service provider computers 114 and/or the data collection device 112 via the networks 408, 412, or via other network connections.

In one illustrative configuration, the user device 102 may include at least one memory 414 and one or more processing units (or processor(s)) 416. The processor(s) 416 may be implemented as appropriate in hardware, computer-executable instructions, firmware, or combinations thereof. Computer-executable instruction or firmware implementations of the processor(s) 416 may include computer-executable or machine-executable instructions written in any suitable programming language to perform the various functions described. The user device 102 may also include geo-location devices (e.g., a global positioning system (GPS) device or the like) for providing and/or recording geographic location information associated with the user device 102.

The memory 414 may store program instructions that are loadable and executable on the processor(s) 416, as well as data generated during the execution of these programs. Depending on the configuration and type of user device 102, the memory 414 may be volatile (such as random access memory (RAM)) and/or non-volatile (such as read-only memory (ROM), flash memory, etc.). The user device 102 may also include additional removable storage and/or non-removable storage 426 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 414 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 414 and the additional storage 426, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 414 and the additional storage 426 are both examples of non-transitory computer storage media. Additional types of computer storage media that may be present in the user device 102 may include, but are not limited to, phase-change RAM (PRAM), SRAM, DRAM, RAM, ROM, electrically erasable programmable read-only memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 102. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 102 may also contain communications connection(s) 428 that allow the user device 102 to communicate with a data store, another computing device or server, user terminals and/or other devices via the networks 408, 412. The user device 102 may also include I/O device(s) 430, such as a keyboard, a mouse, a pen, a voice input device, a touch input device, a display, speakers, a printer, etc.

Turning to the contents of the memory 414 in more detail, the memory 414 may include an operating system 432 and/or one or more application programs or services for implementing the features disclosed herein including an activity pacer module 434, an actual activity module 436, and/or a user interface module 438. In some examples, the activity pacer module 434 may be configured to manage and/or determine (e.g., generate) predicted activity data for the user based at least in part on received probability graphs and/or collected historical data. The activity pacer module 434 may also be configured to operate the activity pacer application 104, which interact with the user interface module 438. In this way, the user device 102 may be able to provide the pacer dot on the user interface 106 whether it determines the predicted data or receives the predicted data. In other words, the activity pacer module 434 may determine predicted data (for the pacer dot) or received predicted data (for the pacer dot).

In some examples, the actual activity module 436 may be configured to work similar to the activity pacer module 434 except that it is for managing the actual (and historic) activity data collected. In some examples, the actual activity module 436 may receive actual activity data collected from the one or more data collection devices or it may collect the actual data on its own (e.g., via sensors of the user device 102). Additionally, like the activity pacer module 434, the actual activity module 436 may be configured provide stored and/or determined to the user interface module 438. In some examples, the actual activity data module 436 may be configured to manage actual activity data for the most current interval of a given time period (e.g., a day) and/or it may be manage actual activity that has accumulated over the given time period (including the current interval). In this way, the actual activity module 436 may know or be able to determine both the current data and the historic data for the day. The data described with reference to this module 436 may be referred to as actual activity data or current activity data because it is data that was actually collected by the user device 102 and/or the data collection device 112 as opposed to predicted data.

The service provider computers 114 may also be any type of computing device such as, but not limited to, a mobile phone, a smartphone, a PDA, a laptop computer, a desktop computer, a thin-client device, a tablet computer, a wearable device, etc. In some examples, the service provider computers 114 may be in communication with the user device 102 and/or the data collection device 112 via the networks 408, 412, or via other network connections.

In one illustrative configuration, the service provider computers 114 may include at least one memory 442 and one or more processing units (or processor(s)) 444. The processor(s) 444 may be implemented as appropriate in hardware, computer-executable instructions, firmware, or combinations thereof. Computer-executable instruction or firmware implementations of the processor(s) 444 may include computer-executable or machine-executable instructions written in any suitable programming language to perform the various functions described.

The memory 442 may store program instructions that are loadable and executable on the processor(s) 444, as well as data generated during the execution of these programs. Depending on the configuration and type of service provider computer 114, the memory 442 may be volatile (such as RAM) and/or non-volatile (such as ROM, flash memory, etc.). The service provider computer 114 may also include additional removable storage and/or non-removable storage 446 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 442 may include multiple different types of memory, such as SRAM, DRAM, or ROM. While the volatile memory described herein may be referred to as RAM, any volatile memory that would not maintain data stored therein once unplugged from a host and/or power would be appropriate. The memory 442 and the additional storage 446, both removable and non-removable, are both additional examples of non-transitory computer-readable storage media.

The service provider computer 114 may also contain communications connection(s) 448 that allow the service provider computer 114 to communicate with a data store, another computing device or server, user terminals and/or other devices via the networks 408, 412. The service provider computer 114 may also include I/O device(s) 450, such as a keyboard, a mouse, a pen, a voice input device, a touch input device, a display, speakers, a printer, etc.

Turning to the contents of the memory 442 in more detail, the memory 442 may include an operating system 452 and/or one or more application programs or services for implementing the features disclosed herein including a prediction module 454. In some examples, the prediction module 454 may be configured to receive actual and/or historic activity data from the user device 102 (e.g., about or otherwise collected from a user). The prediction module 454 may also be configured to generate probability graphs and/or predicted amounts of activity expected to be conducted by the user. In some example the prediction module 454 may provide the probability graph and/or the predicted amount of activity to the user device 102 for presentation to the user as part of the pacer interface 106 of FIG. 1 provided by the user interface module 438.

In some implementations, a client (e.g., one or more modules of the user device 102) can request that the sampling daemon (e.g., the prediction module 454) generate statistics for an attribute or an attribute value. For example, similar to forecast generation, a client can specify a history window over which statistics for an attribute or attribute value should be generated. The sampling daemon may analyze attribute events that occur within the specified history window when generating statistics for the specified attribute or attribute value. The client request can specify which of the following statistics should be generated by the sampling daemon.

In some examples, the sampling daemon can generate a "count" statistic for an attribute or attribute value. For example, the "count" statistic can count the number of events associated with the specified attribute or attribute value that occur within the specified history window.

The sampling daemon can generate statistics based on attribute values. For example, a client can request and the sampling daemon can return the first value and/or the last value for an attribute in the specified history window. A client can request and the sampling daemon can return the minimum, maximum, mean, mode, and standard deviation for all values associated with the specified attribute within the specified history window. The sampling daemon can generate or determine which values are associated with requested percentiles (e.g., 10th, 25th, 50th, 75th, 90th, etc.).

In some cases, the sampling daemon can generate duration statistics. For example, the sampling daemon can determine a duration associated with an attribute value by comparing an attribute's start event with the attribute's stop event. The time difference between when the start event occurred and when the stop event occurred will be the duration of the event. In some implementations, a client can request and the sampling daemon can return the minimum, maximum, mean, mode, or standard deviation for all durations associated with the specified attribute or attribute value within the specified history window. The sampling daemon can generate or determine which duration values are associated with requested percentiles (e.g., 10th, 25th, 50th, 75th, 90th, etc.).

Figure 5:
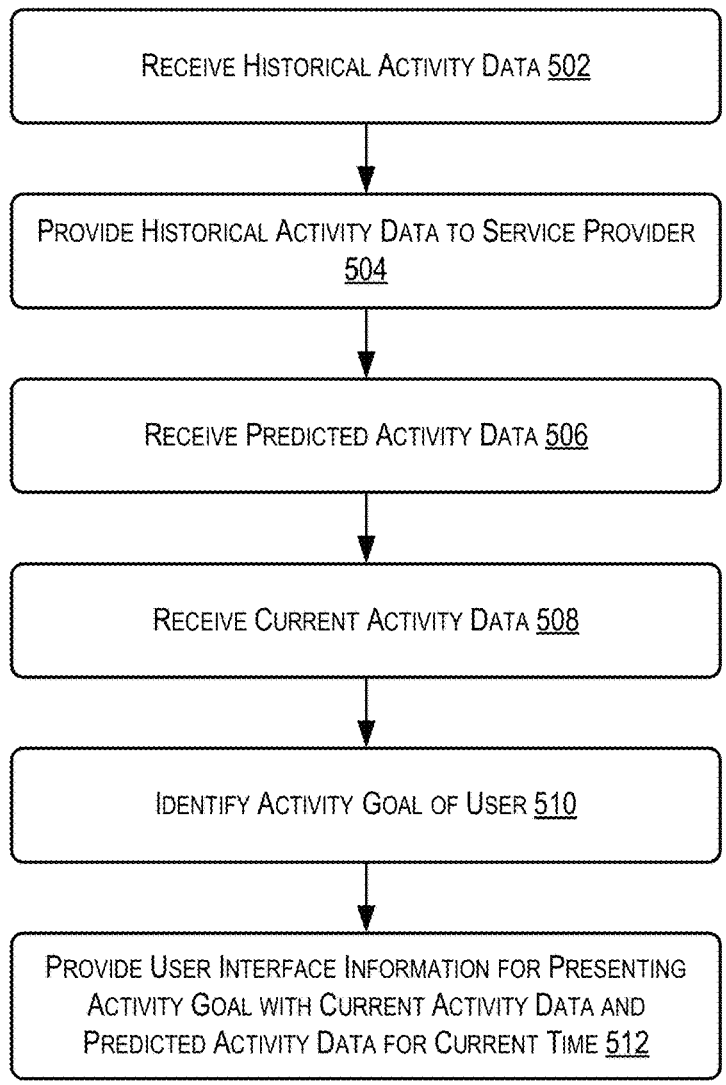
FIG. 5 is a simplified flowchart of an example method for managing pacer activity data of a user as described herein, according to at least one example.
Figure 6:
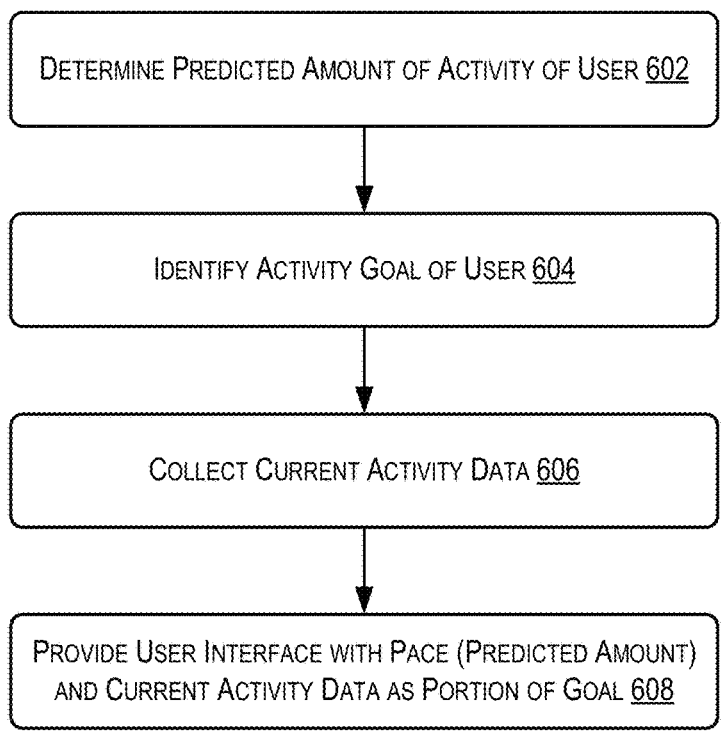
FIG. 6 is a simplified flowchart of another example method for managing pacer activity data of a user as described herein, according to at least one example.
Figure 7:
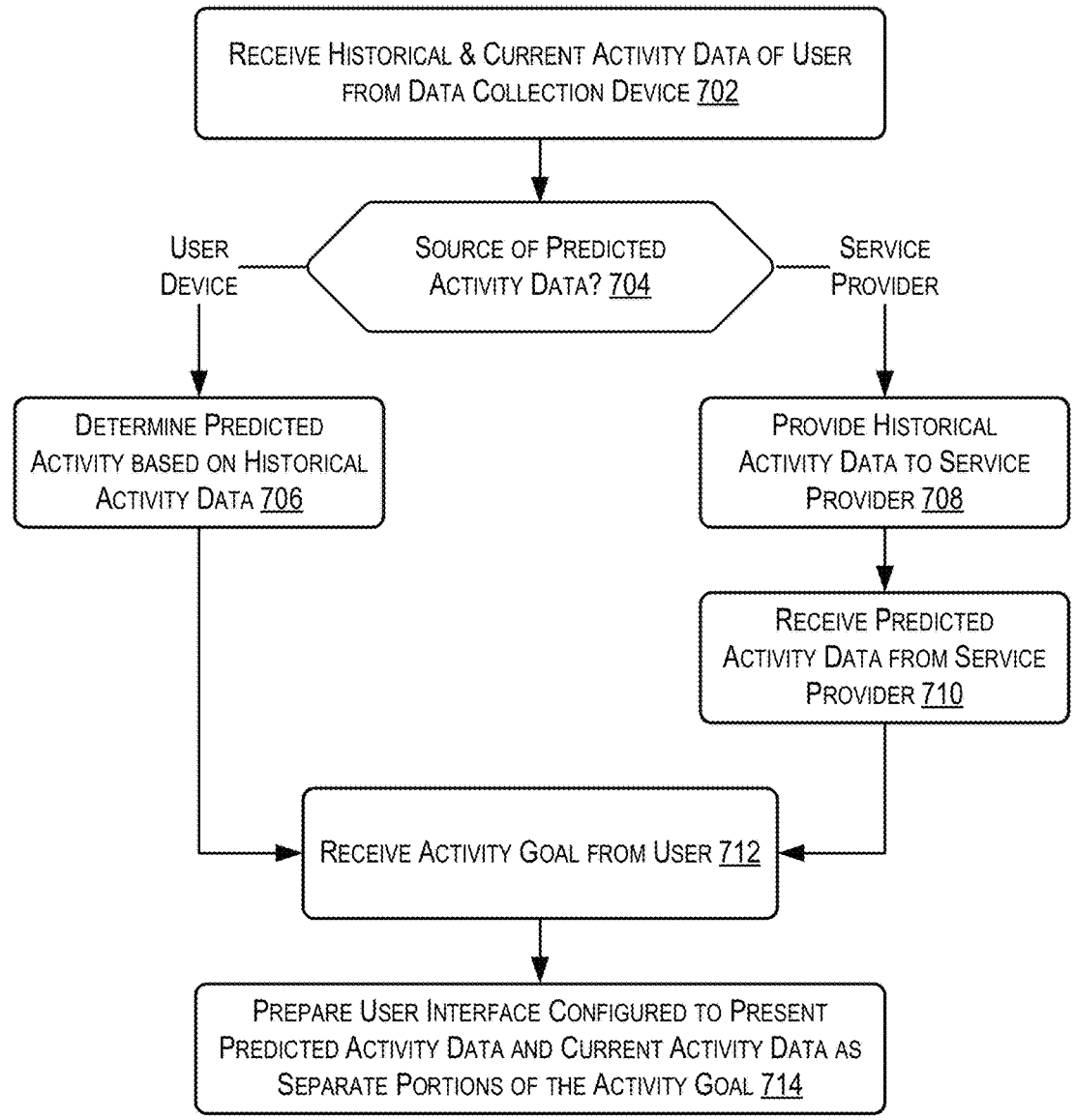
FIG. 7 is a simplified flowchart of another example method for managing pacer activity data of a user as described herein, according to at least one example.

FIGS. 5-7 illustrate example flow diagrams showing processes 500, 600, and 700 for providing and/or managing pacing activity data of a user, according to at least a few embodiments. In some examples, the user device 102 (e.g., utilizing at least the activity pacer module 434 shown in FIG. 4) may perform the process 500 of FIG. 5. The process 500 may begin at 502 where the user device 102 may receive historical activity data of a user. This historical activity data may be of a cumulative type such as calories burned, amount of time exercised, number of steps walked or ran, etc. The historical data may be collected over a period of time (e.g., hours, days, weeks, etc.). Additionally, in some examples, the historical activity data may be received from a data collection device (e.g., a heart rate monitor, a calorie tracker, or the like). At 504, the user device 102 may provide the historical activity data to a service provider (e.g., a third-party application and/or computing system). The service provider may be configured to determine predicted activity data for the user. In some cases the predicted activity data may comprise a probability for each interval of time within a range (e.g., each hour of a day, each day of a week, etc.). At 506, the user device 102 may receive the predicted activity data from the service provider.

At 508 or throughout the process 500, the user device 102 may also receive current and/or collected activity data. This current activity data may be received, in some examples, from the data collection device that provided the historical activity data or a separate data collection device. Alternatively, the historical activity data received at 502 may be stored locally and received from the local data store as opposed to being received from the data collection device. In any event, the current activity data collected at 508 may include a cumulative amount of activity data for the day (e.g., total calories burned thus far) or it may include the most current collected data (in which case, the user device 102 may accumulate the current activity data with previously received activity data to determine the cumulative amount of collected data for the time period). At 510, the user device 102 may identify an activity goal of the user (which may be configured by the user and saved in local or remote memory). At 512, the user device 102 may provide a user interface (e.g., the interface 106 of FIG. 1, 201 of FIG. 2, or 302 of FIG. 3) for presenting the activity goal with the current activity data (e.g., cumulative amount up to the current time) and the predicted data for the current time.

FIG. 6 illustrates another process 600 for providing and/or managing pacing activity data of a user, according to at least a few embodiments. In some examples, the user device 102 (e.g., utilizing at least the activity pacer module 434 shown in FIG. 4) may perform the process 600 of FIG. 6. The process 600 may begin at 602 where the user device 102 may determine a predicted amount of activity of a user based at least in part on historical activity data. At 604, the user device 102 may identify an activity goal of the user and at 606, the user device collect current activity data of the user (e.g., actual activity data for a specific point in time and/or cumulative activity data over an interval of time). Further, the user device may provide a user interface with a pace (e.g., based at least in part on the predicted amount of activity data) and the current cumulative amount of activity data as a portion (e.g., a percentage or subset) of the identify activity goal of the user at 608.

FIG. 7 illustrates another process 700 for providing and/or managing pacing activity data of a user, according to at least a few embodiments. In some examples, the user device 102 (e.g., utilizing at least the activity pacer module 434 shown in FIG. 4) may perform the process 700 of FIG. 7. The process 700 may begin at 702 where the user device 102 may receive historical and current activity data of a user. The historical activity data and/or the current activity data may be cumulative or a particular period or interval of time, and it may be received from a data collection device such as a pedometer, a calorie tracker, or the like. At 704, the user device 102 may determine the source of predicted activity data of the user. In some examples, the predicted activity data may be received from a service provider. However, in other examples, the predicted data may be determined locally at the user device 102, in which case the user device 102 may be the source of the predicted data. In general, the predicted data may be in the form of a probability and may be based at least in part on the historical activity data of the user.

If the user device 102 is to the be source of the predicted data, the user device 102 may determine the predicted activity data based at least in part on the historical activity data at 706. However, if the service provider is the source of the predicted activity data, the user device 102 may first provide the historical activity data to the service provider at 708, and then receive the predicted activity data from the service provider at 710. At 712, the user device 102 may receive or other identify an activity goal of the user (e.g., from the user). Further, in some examples, at 714, the user device 102 may prepare a user interface configured to present the predicted activity data and the current activity data as separate portions of the activity goal. For example, the predicted activity data may identify a cumulative predicted amount of calories burned with respect to the goal, while at the same time (or at least within the same interface), the current or actual activity data may identify a cumulative actual amount of calories burned with respect to the goal.

Figure 8:
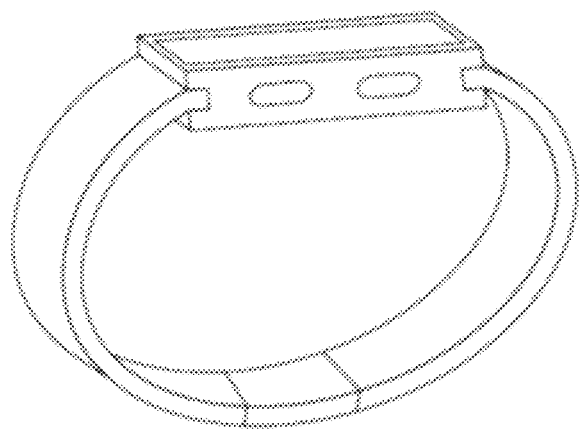
FIG. 8 is a simplified block diagram illustrating example devices for managing pacer activity data of a user as described herein, according to at least one example.

Embodiments described herein may take the form of, be incorporated in, or operate with a suitable electronic device. One example of such a device is shown in FIG. 8 and takes the form of a wearable mechanism. As shown, the mechanism may be worn on a user's wrist and secured thereto by a band. The mechanism may have a variety of functions including, but not limited to: keeping time; monitoring a user's physiological signals and providing health-related information based on those signals; communicating (in a wired or wireless fashion) with other electronic devices, which may be different types of devices having different functionalities; providing alerts to a user, which may include audio, haptic, visual and/or other sensory output, any or all of which may be synchronized with one another; visually depicting data on a display; gather data form one or more sensors that may be used to initiate, control, or modify operations of the device; determine a location of a touch on a surface of the device and/or an amount of force exerted on the device, and use either or both as input; accepting voice input to control one or more functions; accepting tactile input to control one or more functions; and so on.

Alternative embodiments of suitable electronic devices include a phone; a tablet computing device; a portable media player; and so on. Still other suitable electronic devices may include laptop/notebook computers, personal digital assistants, touch screens, input-sensitive pads or surfaces, and so on.

Figure 9:
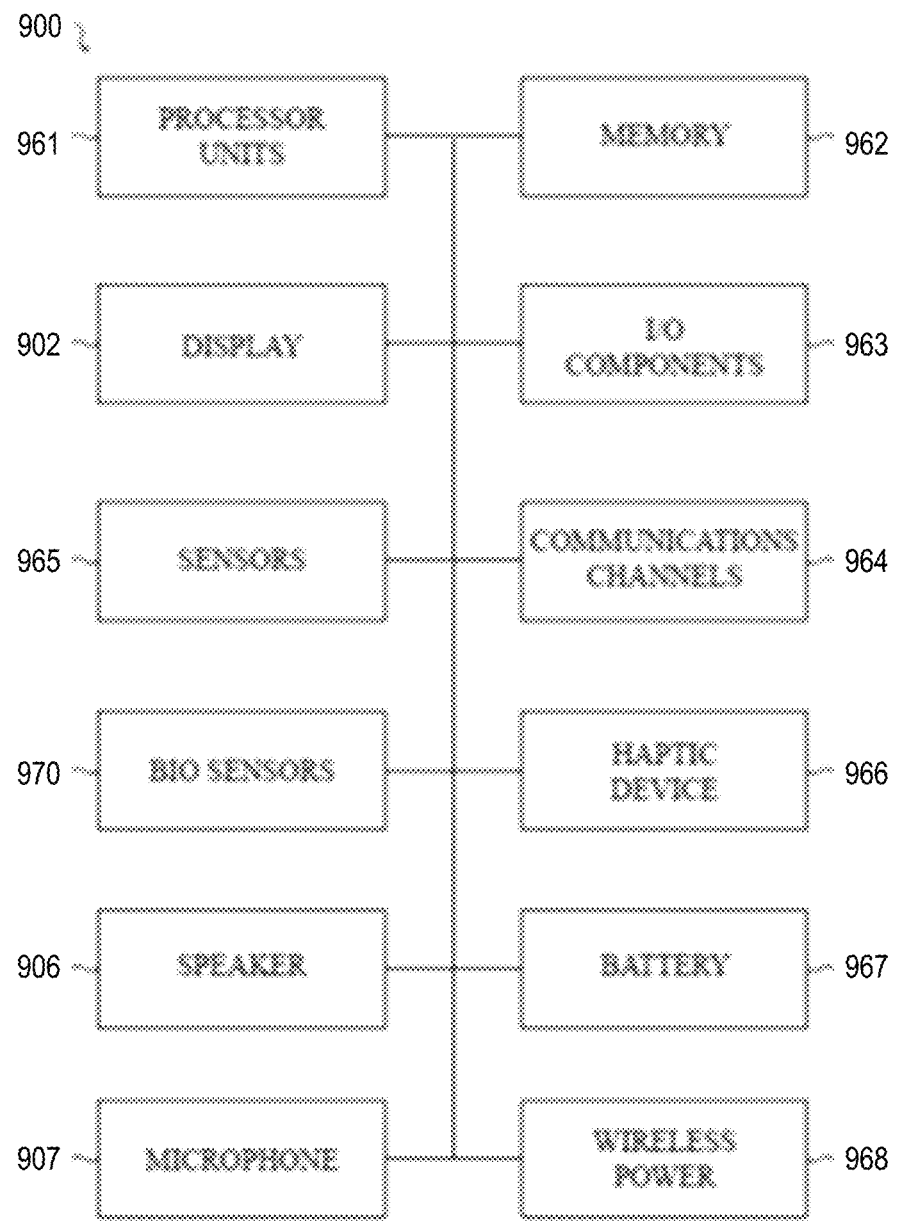
FIG. 9 is a simplified block diagram illustrating another example architecture for managing pacer activity data of a user as described herein, according to at least one example.

FIG. 9 depicts an example schematic diagram of a wearable electronic device. As shown in FIG. 9, the device 900 includes one or more processing units 961 that are configured to access a memory 962 having instructions stored thereon. The instructions or computer programs may be configured to perform one or more of the operations or functions described with respect to the device 900. For example, the instructions may be configured to control or coordinate the operation of the various components of the device. Such components include, but are not limited to, display 902, one or more input/output components 963, one or more communication channels 964, one or more sensors 965, a speaker 906, microphone 907, and/or one or more haptic feedback devices 966. In some embodiments the speaker and microphone may be combined into a single unit and/or may share a common port through a housing of the device.

The processing units 961 of FIG. 9 may be implemented as any electronic device capable of processing, receiving, or transmitting data or instructions. For example, the processing units 961 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

In some embodiments the electronic device may accept a variety of bands, straps, or other retention mechanisms (collectively, "bands"). These bands may be removably connected to the electronic device by a lug that is accepted in a recess or other aperture within the device and locks thereto. The lug may be part of the band or may be separable (and/or separate) from the band. Generally, the lug may lock into the electronic device's recess and thereby maintain connection between the band and device. The user may release a locking mechanism to permit the lug to slide or otherwise move out of the recess. In some embodiments, the recess may be formed in the band and the lug may be affixed or incorporated into the device.

A user may change combinations of bands and electronic devices, thereby permitting mixing and matching of the two categories. It should be appreciated that devices having other forms and/or functions may include similar recesses and may releasably mate with a lug and/or band incorporating a lug. In this fashion, an ecosystem of bands and devices may be envisioned, each of which is compatible with another. A single band may be used to connect to devices, as one further example; in such embodiments the band may include electrical interconnections that permit the two devices to transmit signals to one another and thereby interact with one another.

In many embodiments, the electronic device may keep and display time, essentially functioning as a wristwatch among other things. Time may be displayed in an analog or digital format, depending on the device, its settings, and (in some cases) a user's preferences. Typically, time is displayed on a digital display stack forming part of the exterior of the device.

The display stack may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some embodiments.

The device also may comprise one or more touch sensors to determine a location of a touch on the cover glass. A touch sensor may be incorporated into or on the display stack in order to determine a location of a touch. The touch sensor may be self-capacitive in certain embodiments, mutual-capacitive in others, or a combination thereof.

Similarly, the device may include a force sensor to determine an amount of force applied to the cover glass. The force sensor may be a capacitive sensor in some embodiments and a strain sensor in other embodiments. In either embodiment, the force sensor is generally transparent and made form transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one embodiment the force sensor may take the form of a gasket extending beneath the periphery of the display. The gasket may be segmented or unitary, depending on the embodiment.

The electronic device may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative embodiments the haptic actuator may be rotary or any other type). A speaker may provide auditory components of an alert and the aforementioned display may provide visual alert components. In some embodiments a dedicated light, display, or other visual output component may be used as part of an alert.

The auditory, haptic and/or visual components of the alert may be synchronized to provide an overall experience to a user. One or more components may be delayed relative to other components to create a desired synchronization between them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output but at a weak or even subliminal level, thereby priming the wearer to receive the auditory output.

Figure 10:
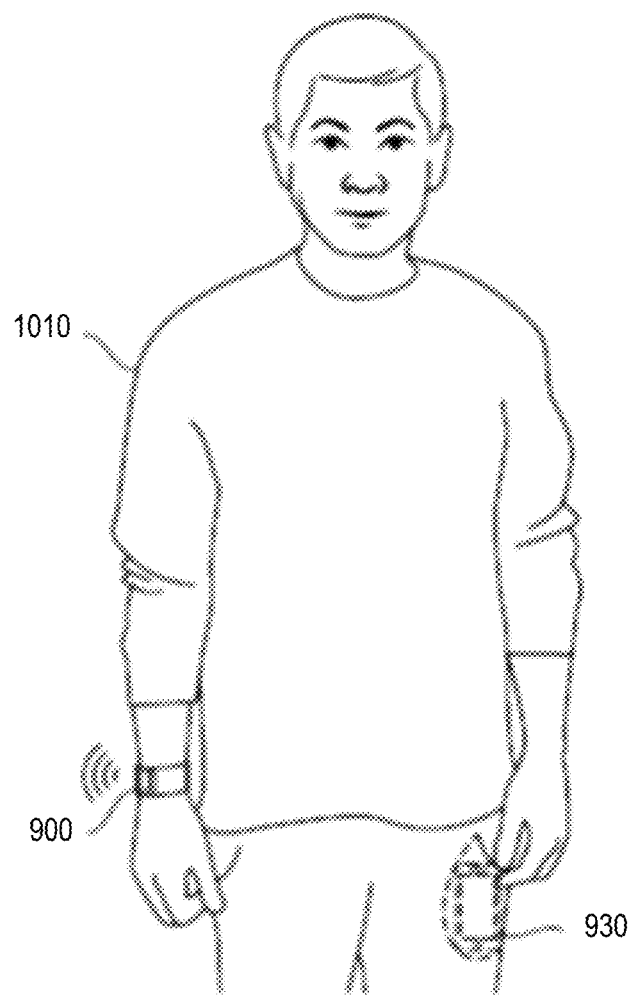
FIG. 10 is a simplified block diagram illustrating additional example devices for managing pacer activity data of a user as described herein, according to at least one example.

The example electronic device may communicate with other electronic devices either through a wired connection or wirelessly. Data may be passed between devices, permitting one device to relay information to another; control another; employ another's sensors, outputs, and/or inputs; and so on. FIG. 10 depicts a user 1010 wearing a sample electronic device 900 with a second electronic device 930 in his pocket. Data may be wirelessly transmitted between the electronic devices 900, 930, thereby permitting the user 1010 to receive, view, and interact with data from the second device 930 by means of the first electronic device 900. Thus, the user 1010 may have access to part or all of the second device's functionality through the first electronic device 900 without actually needing to interact directly with the second device 930.

Further, the electronic devices 900, 930 may cooperate not only to share data but to share functionality as well. For example, one of the two devices may incorporate a sensor, application, or function that the other lacks. The electronic device lacking such capabilities may request them from the other device, which may share wirelessly with the requesting device. Thus, multiple devices may operate together to provide expanded functions, software, access and the like between the two and ultimately to a user. As one non-limiting example, the electronic device 900 may be unable to place or receive telephone calls while the second device 930 may be able to do so. A user may nonetheless make and/or receive calls through the first device 900, which may employ the second device 930 to actually place or accept a call.

As another non-limiting example, an electronic device 900 may wirelessly communicate with a sales terminal nearby, thus permitting a user to quickly and efficiently conduct a transaction such as selling, buying, or returning a good. The electronic device may use near field communications technology to perform these and other functions.

As mentioned above, a band may be connected to two electronic devices and may serve as a wired communication path between the two. As another example, the devices may communicate wirelessly, thereby permitting one device to relay information from a second to a user. This latter example may be particularly useful when the second is inaccessible.

Certain embodiments may incorporate one or more biometric sensors to measure certain physiological characteristics of a user. The device may include a photoplesymogram sensor to determine a user's heart rate or blood oxygenation levels, for example. The device may also or instead include electrodes to measure the body impedance of a user, which may permit the device to estimate body fat percentages, the body's electrical activity, body impedance, and so on. Also include blood pressure, ultraviolet exposure, etc. Depending on the sensors incorporated into or associated with the electronic device, a variety of user characteristics may be measured and/or estimated, thereby permitting different health information to be provided to a user. In some examples, the sensed biometric data may be used, in part, to determine the historic, current, and/or predicted activity data of the user.

Certain embodiments may be wirelessly charged. For example, an inductive charging base may transmit power to an inductive receiver within the device in order to charge a battery of the device. Further, by varying the inductive field between the device and base, data may be communicated between the two. As one simple non-limiting example, this may be used to wake the base from a low-power sleep state to an active charging state when the device is placed on the base. Other wireless charging systems also may be used (e.g., near field magnetic resonance and radio frequency). Alternatively, the device also may employ wired charging through electrodes.

In certain embodiments, the device may include a rotary input, which may take the form of a crown with a stem. The crown and stem may be rotated to provide the rotary input. Rotation of the stem and/or crown may be sensed optically, electrically, magnetically, or mechanically. Further, in some embodiments the crown and stem may also move laterally, thereby providing a second type of input to the device.

The electronic device may likewise include one or more buttons. The button(s) may be depressed to provide yet another input to the device. In various embodiments, the button may be a dome switch, rocker switch, electrical contact, magnetic switch, and so on. In some embodiments the button may be waterproof or otherwise sealed against the environment.

Various embodiments may include or otherwise incorporate one or more motion sensors. A motion sensor may detect motion of the device and provide, modify, cease, or otherwise affect a state, output, or input of the device or associated applications based on the motion. As non-limiting examples, a motion may be used to silence the device or acknowledge an alert generated by the device. Sample motion sensors include accelerometers, gyroscopic sensors, magnetometers, GPS sensors, distance sensors, and so on. Some embodiments may use a GPS sensor to facilitate or enable location and/or navigation assistance.

As shown in FIG. 9, the device 900 may also include one or more acoustic elements, including a speaker 906 and/or a microphone 907. The speaker 906 may include drive electronics or circuitry and may be configured to produce an audible sound or acoustic signal in response to a command or input. Similarly, the microphone 907 may also include drive electronics or circuitry and is configured to receive an audible sound or acoustic signal in response to a command or input. The speaker 906 and the microphone 907 may be acoustically coupled to port or opening in the case that allows acoustic energy to pass, but may prevent the ingress of liquid and other debris.

Certain embodiments may incorporate an ambient light sensor. The ambient light sensor may permit the device to sense a brightness of its environment and adjust certain operational parameters accordingly. For example, the electronic device may modify a brightness of a display in response to the sensed ambient light. As another example, the electronic device may turn the display off if little or no light is sensed for a period of time.

These and other functions, operations, and abilities of the electronic device will be apparent upon reading the specification in its entirety.

Certain embodiments of a wearable electronic device may include one or more sensors that can be used to calculate a health metric or other health-related information. As one example, a wearable electronic device may function as a wearable health assistant that provides health-related information (whether real-time or not) to the user, authorized third parties, and/or an associated monitoring device.

Figure 11:
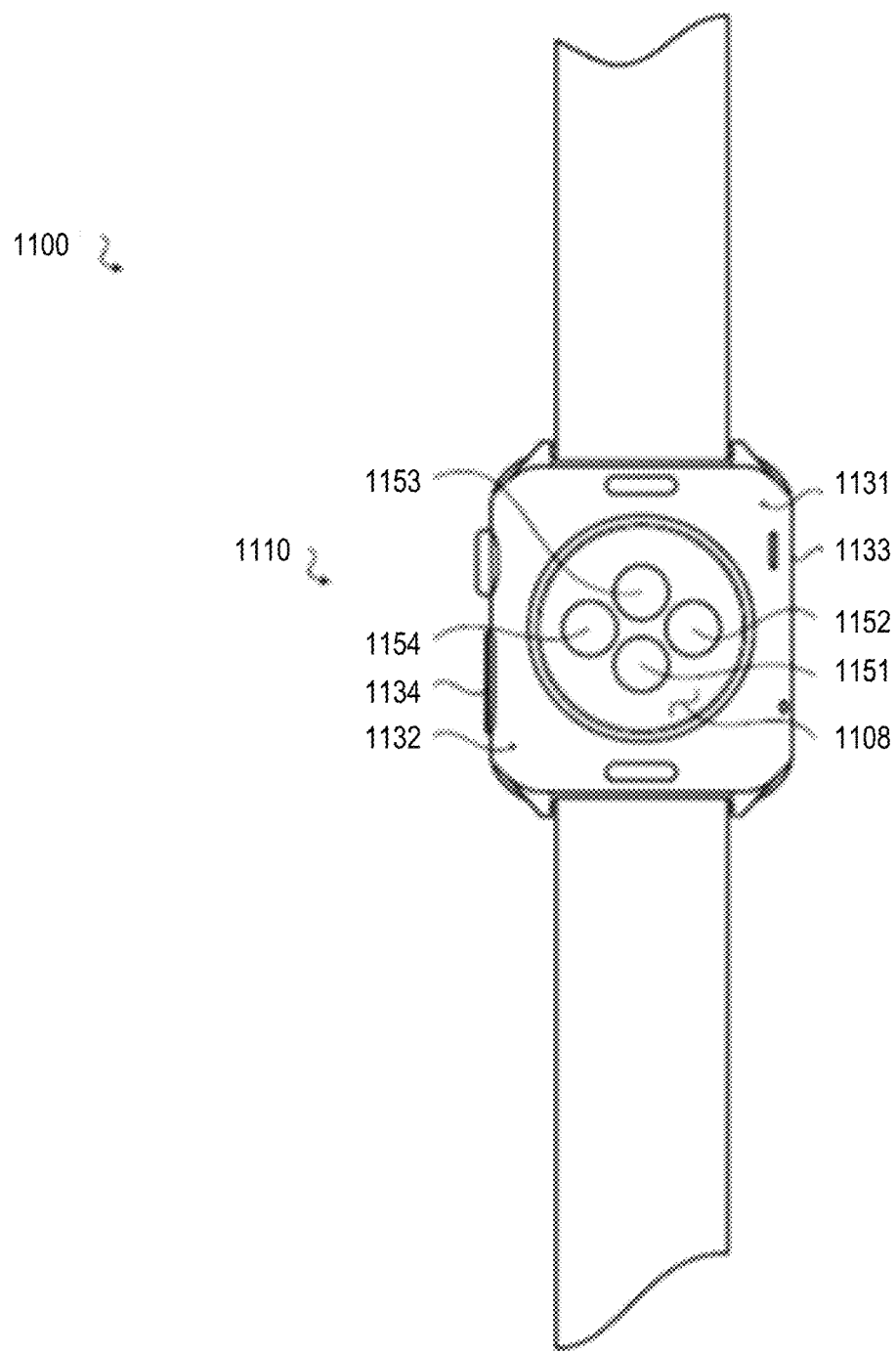
FIG. 11 is a simplified block diagram illustrating an additional example device for managing pacer activity data of a user as described herein, according to at least one example.

FIG. 11 depicts an example electronic device having one or more biometric sensors. As shown in FIG. 11, an array of light sources and a photodetector 1151-1154 may be disposed on the rear surface of the device 100. In one example, the light sources 1151-1153 are formed from light emitting diode (LED) elements that are configured to emit light into a portion of the wearer's body (e.g., wrist). The photodetector 1154 is shared between the multiple light sources 1151-1153 and is configured to receive light reflected from the body. The photodetector may be formed from a photodiode material that is configured to produce a signal based on the received light. In one implementation, the signal produced by the photodetector 1154 is used to compute a health metric associated with the wearer. In some cases, the light sources 1151-1153 and the photodetector 1154 form a photoplethysmography (PPG) sensor. The first light source 1151 may include, for example, a green LED, which may be adapted for detecting blood perfusion in the body of the wearer. The second light source 1152 may include, for example, an infrared LED, which may be adapted to detect changes in water content or other properties of the body. The third 1153 light source may be a similar type or different types of LED element, depending on the sensing configuration. The optical (e.g., PPG) sensor or sensors may be used to compute various health metrics, including, without limitation, a heart rate, a respiration rate, blood oxygenation level, a blood volume estimate, blood pressure, or a combination thereof. One or more of the light sources 1151-1153 and the photodetector 1154 may also be used for optical data transfer with a base or other device. While FIG. 11 depicts one example embodiment, the number of light sources and/or photodetectors may vary in different embodiments. For example, another embodiment may use more than one photodetector. Another embodiment may also use fewer or more light sources than are depicted in the example of FIG. 11.

Also as shown in FIG. 11, the device 1100 includes multiple electrodes 1131, 1132, 1133, 1134 that are located on or near external surfaces of the device 1100. In the present example, the device 1100 includes a first electrode 1131 and a second electrode 1132 that are located on or proximate to a rear-facing surface of the device body 1110. In this example, the first electrode 1131 and the second electrode 1132 are configured to make electrical contact with the skin of the user wearing the device 1100. In some cases, the first 1131 and second 1132 electrodes are used to take an electrical measurement or receive an electrical signal from the body of the user. As also shown in FIG. 11, the device 1100 may include a third electrode 1133 and a fourth electrode 1134 that are located on or proximate to a perimeter of the case 1101 of the device body 1110. In the present example, the third 1133 and fourth 1134 electrodes are configured to be contacted by one or more fingers of the user who is wearing or interacting with the device 1100. In some cases, the third 1133 and fourth 1134 electrodes are also used to take an electrical measurement or receive an electrical signal from the body of the user. In some cases, the first 1131, second 1132, third 1133, and fourth 1134 electrodes are all used to take a measurement or series of measurements that can be used to compute another health metric of the user's body. Health metrics that may be computed using the electrodes include, without limitation, heart functions (ECG, EKG), water content, body-fat ratios, galvanic skin resistance, and combinations thereof.

In the configuration depicted in FIG. 11, the electronic device 1100 includes one or more apertures in the case 1101. A light source 1151-1155 may be disposed in each aperture. In one embodiment, each light source 1151-1153 is implemented as a light-emitting diode (LED). In the present example, the four apertures, three light sources 1151-1153 and a single detector 1155 are used to form one or more sensors. Other embodiments can include any number of light sources. For example, two light sources can be used in some embodiments.

The light sources may operate at the same light wavelength range, or the light sources can operate at different light wavelength ranges. As one example, with two light sources one light source may transmit light in the visible wavelength range while the other light source can emit light in the infrared wavelength range. With four light sources, two light sources may transmit light in the visible wavelength range while the other two light sources can emit light in the infrared wavelength range. For example, in one embodiment, at least one light source can emit light in the wavelength range associated with the color green while another light source transmits light in the infrared wavelength range. When a physiological parameter of the user is to be determined, the light sources emit light toward the user's skin and the optical sensor senses an amount of reflected light. In some cases, a modulation pattern or sequence may be used to turn the light sources on and off and sample or sense the reflected light.

Illustrative methods and systems for managing user device connections are described above. Some or all of these systems and methods may, but need not, be implemented at least partially by architectures such as those shown at least in FIGS. 1-11 above. While many of the embodiments are described above with reference to personal, activity, and/or health-related information, it should be understood that any type of user information or non-user information (e.g., data of any type) may be managed using these techniques. Further, in the foregoing description, various non-limiting examples were described. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a network server, the network server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more applications that may be implemented as one or more scripts or programs written in any programming language, such as Java®, C, C#or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen or keypad), and at least one output device (e.g., a display device, printer or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable media for containing code, or portions of code, can include any appropriate media known or used in the art, including storage media, such as but not limited to volatile and non-volatile, removable and non-removable media implemented in any method or technology for storage of information such as computer-readable instructions, data structures, program modules or other data, including RAM, ROM, Electrically Erasable Programmable Read-Only Memory (EEPROM), flash memory or other memory technology, CD-ROM, DVD or other optical storage, magnetic cassettes, magnetic tape, magnetic disk storage or other magnetic storage devices or any other medium which can be used to store the desired information and which can be accessed by the a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method, comprising:
   receiving, by a first computing device, historical activity data of a user from a second computing device configured to collect the historical activity data;
   providing, by the first computing device, the received historical activity data to a service provider configured to determine a predicted amount of activity data for an interval of time of the user;
   receiving, from the service provider, the predicted amount of activity data for an identified interval of time;
   receiving, by the first computing device, current activity data of the user collected by the second computing device during a current interval of time that corresponds to the identified interval of time;
   identifying an activity goal of the user; and
   providing, to the second computing device, information for configuring a user interface of the second computing device to present the activity goal, the current activity data for the current interval, the predicted amount of activity data for the current interval, and a pace indicator that identifies predicted cumulative progress towards the activity goal, wherein the pace indicator moves on the user interface as the predicted amount of activity of the user changes for the current interval.

2. The computer-implemented method of claim 1, wherein the user interface of the second computing device is configured to present a first graphical representation of the current activity data and the predicted amount of activity data overlaid on a second graphical representation of the activity goal.

3. The computer-implemented method of claim 2, wherein the first graphical representation is configured to present the current activity data adjacent to the predicted amount of activity data.

4. The computer-implemented method of claim 1, wherein the current interval comprises an hour of a day in which the current activity data is detected.

5. The computer-implemented method of claim 1, wherein the historical activity data comprises calories burned by the user, heart beats of the user, steps walked by the user, distance traveled by the user, or minutes exercised by the user.

6. The computer-implemented method of claim 1, wherein the activity goal of the user is configured by the user.

7. The computer-implemented method of claim 1, wherein the current activity data of the user is collected by a third computing device during the current interval of time that corresponds to the identified interval of time.

8. A non-transitory computer-readable storage medium storing computer-executable instructions that, when executed by a processor, configure the processor to perform operations comprising:
receiving, by a first computing device, historical activity data of a user from a second computing device configured to collect the historical activity data;
providing, by the first computing device, the received historical activity data to a service provider configured to determine a predicted amount of activity data for an interval of time of the user;
receiving, from the service provider, the predicted amount of activity data for an identified interval of time;
receiving, by the first computing device, current activity data of the user collected by the second computing device during a current interval of time that corresponds to the identified interval of time;
identifying an activity goal of the user; and
providing, to the second computing device, information for configuring a user interface of the second computing device to present the activity goal, the current activity data for the current interval, the predicted amount of activity data for the current interval, and a pace indicator that identifies predicted cumulative progress towards the activity goal, wherein the pace indicator moves on the user interface as the predicted amount of activity of the user changes for the current interval.

9. The non-transitory computer-readable storage medium of claim 8, wherein the user interface of the second computing device is configured to present a first graphical representation of the current activity data and the predicted amount of activity data overlaid on a second graphical representation of the activity goal.

10. The non-transitory computer-readable storage medium of claim 9, wherein the first graphical representation is configured to present the current activity data adjacent to the predicted amount of activity data.

11. The non-transitory computer-readable storage medium of claim 8, wherein the current interval comprises an hour of a day in which the current activity data is detected.

12. The non-transitory computer-readable storage medium of claim 8, wherein the historical activity data comprises calories burned by the user, heart beats of the user, steps walked by the user, distance traveled by the user, or minutes exercised by the user.

13. The non-transitory computer-readable storage medium of claim 8, wherein the activity goal of the user is configured by the user.

14. A system, comprising:
a memory configured to store computer-executable instructions; and
a processor in communication with the memory configured to execute the computer-executable instructions to at least:
receive, by a first computing device, historical activity data of a user from a second computing device configured to collect the historical activity data;
provide, by the first computing device, the received historical activity data to a service provider configured to determine a predicted amount of activity data for an interval of time of the user;
receive, from the service provider, the predicted amount of activity data for an identified interval of time;
receive, by the first computing device, current activity data of the user collected by the second computing device during a current interval of time that corresponds to the identified interval of time;
identify an activity goal of the user; and
provide, to the second computing device, information for configuring a user interface of the second computing device to present the activity goal, the current activity data for the current interval, the predicted activity data for the current interval, and a pace indicator that identifies predicted cumulative progress towards the activity goal, wherein the pace indicator moves on the user interface as the predicted amount of activity of the user changes for the current interval.

15. The system of claim 14, wherein the user interface of the second computing device is configured to present a first graphical representation of the current activity data and the predicted amount of activity data overlaid on a second graphical representation of the activity goal.

16. The system of claim 15, wherein the first graphical representation is configured to present the current activity data adjacent to the predicted amount of activity data.

17. The system of claim 14, wherein the current interval comprises an hour of a day in which the current activity data is detected.

18. The system of claim 14, wherein the historical activity data comprises calories burned by the user, heart beats of the user, steps walked by the user, distance traveled by the user, or minutes exercised by the user.

19. The system of claim 14, wherein the activity goal of the user is configured by the user.

20. The system of claim 14, further comprising a third computing device configured to collect the current activity data of the user during the current interval of time that corresponds to the identified interval of time.

\* \* \* \* \*